United States Patent
Kappler et al.

(10) Patent No.: US 10,182,774 B2
(45) Date of Patent: Jan. 22, 2019

(54) SPECTRAL FILTRATION OF X-RAYS FOR ENERGY-SELECTIVE X-RAY IMAGING

(71) Applicant: Siemens Healthcare GmbH, Erlangen (DE)

(72) Inventors: Steffen Kappler, Effeltrich (DE); Christoph Polster, Erlangen (DE); Stefan Ulzheimer, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 156 days.

(21) Appl. No.: 15/246,622

(22) Filed: Aug. 25, 2016

(65) Prior Publication Data

US 2017/0071559 A1    Mar. 16, 2017

(30) Foreign Application Priority Data

Sep. 11, 2015    (DE) .................. 10 2015 217 421

(51) Int. Cl.
| | | |
|---|---|---|
| A61B 6/03 | (2006.01) | |
| A61B 6/00 | (2006.01) | |
| G21K 1/10 | (2006.01) | |

(52) U.S. Cl.
CPC ............. *A61B 6/4035* (2013.01); *G21K 1/10* (2013.01)

(58) Field of Classification Search
None
See application file for complete search history.

(56) References Cited

U.S. PATENT DOCUMENTS 7,076,029 B2 *    7/2006    Toth .................. A61B 6/032
378/158

2003/0103598 A1 *    6/2003    Bogatu .............. A61B 6/4042
378/157
2006/0182226 A1    8/2006    Yuan
2009/0225944 A1 *    9/2009    Lee .................. G01N 23/2076
378/71
2013/0108024 A1 *    5/2013    Parsons .................. H01J 35/08
378/121

FOREIGN PATENT DOCUMENTS

DE        10227808 A1     1/2004
DE        102012011309 A1    5/2013

OTHER PUBLICATIONS

Spahn Martin, "Flat detectors and their clinical applications", European Radiology, vol. 15, 2005, pp. 1934-1947, DOI:10.1007/s00330-005-2734-9.
Taguchi K.: "Vision 20/20: Single photon counting x-ray detectors in medical imaging", in Med. Phys. vol. 40, No. 10, pp. 1009011-10090119 / Dec. 9, 2013.
German Office Action dated Feb. 16, 2016.

* cited by examiner

*Primary Examiner* — Hoon Song
(74) *Attorney, Agent, or Firm* — Harness, Dickey & Pierce, P.L.C.

(57) ABSTRACT

A filter is disclosed for the spectral filtration of X-rays emanating from an X-ray source which cross an object under examination and are detected by an X-ray detector in at least two different spectral regions. After crossing the object under examination, the X-rays have an energy spectrum which displays a characteristic distribution for the anode material of the X-ray source. In an embodiment, the filter is configured to suppress part of the energy spectrum comprising the focal point of the energy spectrum. A corresponding X-ray system and method are also disclosed.

22 Claims, 4 Drawing Sheets

SPECTRAL FILTRATION OF X-RAYS FOR ENERGY-SELECTIVE X-RAY IMAGING

PRIORITY STATEMENT

The present application hereby claims priority under 35 U.S.C. § 119 to German patent application number DE 102015217421.2 filed Sep. 11, 2015, the entire contents of which are hereby incorporated herein by reference.

FIELD

At least one embodiment of the invention generally relates to a filter for the spectral filtration of X-rays emanating from an X-ray source which are detected with an energy-selective X-ray detector in at least two different spectral regions. In at least one embodiment, the filter is configured to suppress part of the energy spectrum of the X-rays more strongly than other partial areas of the X-ray spectrum. This results in optimized spectral resolution of the signals detected by the X-ray detector. At least one embodiment of the invention also generally relates to a corresponding X-ray system and method.

BACKGROUND

X-ray imaging and, in particular, computer tomography systems enable spectral imaging via traditional energy-integrating X-ray detectors, by examining an object under examination, as a rule a patient, using two divergent X-ray spectra. This can, for example, be performed via two X-ray sources operating in parallel or via fast kV switching at only one X-ray source. Typically, an 80-kV spectrum and a 140-kV spectrum can be used.

In addition, the spectral separation of the energy spectra can be reinforced by way of corresponding pre-filtering, e.g. with dual-energy imaging with the X-ray source which is operated with a higher tube voltage of, for example, 140 kV, a tin filter is regularly used to clean the energy spectrum of the X-ray source of low-energy photons. Inherent in this method is the temporal and/or spatial separation of measurements, with the consequence that known algorithms for material breakdown can only operate in the image space.

In contrast, spectrally sensitive X-ray detectors permit the simultaneous recording of X-ray attenuation data in one and the same projection direction with regard to an object under examination in two or more different spectral regions. In principle, this enables flexible further processing of the X-ray attenuation data and can also advantageously reduce the dose to which the patient is exposed. However, the spectral detector response function of an actual, spectrally sensitive, photon-counting X-ray detector is not perfect as it is impaired by physical and electronic effects. These include, inter alia, in particular the effects of pulse pileup, charge sharing, K-escape, Compton scattering and charge trapping.

With pulse pileup, photons striking the detector are simultaneously or quasi-coincidently converted into overlapping pulses which are detected as a resulting pulse of correspondingly higher energy and result in the loss of a counting signal. With charge sharing, a charge cloud generated by an incident photon is at least partially transferred to one or more adjacent pixels in the detector material. As a result, counting signals in different pixels are detected by a photon in energies below the quantum energy of the incident photon.

If a hole generated by an incident photon for each photoelectric effect on an inner shell of an atom of the detector material is filled up by an electron of a higher shell, characteristic radiation in the form of (fluorescent) X-rays of the corresponding K-junction is released. At best, this radiation causes a pulse pileup in the same pixel. But due to its stochastic directional distribution, it may also be detected in another pixel or not at all. In both the aforementioned cases, the counting signals are distorted.

The Compton effect, in which the photons undergoing a change of direction only deposit a portion of their energy in the detector material, results in a false detection site, insufficient detected energy and/or no detection of this photon at all. As a result of impurities or lattice defects in the detector material, charges generated with charge trapping may be trapped and only detected with reduced energy with a time lag. In short, the counting signals emitted by the counting X-ray detector in the individual energy bins or energy windows only partially correspond to the actual incident X-rays on the detector in these energy fields. This results in the spectral resolution of adjacent spectral regions of the incident energy spectrum being impaired so that they can only be mapped insufficiently or not at all. As a result, the basic "high-energy capacity" and in particular the "dual-energy capacity" of a spectrally sensitive X-ray detector is limited.

In addition, there are currently many applications and/or examinations by way of X-ray imaging in the ultra-low dosage range. These are applications which are or must be performed with a lower X-ray dose applied to the object under examination than would be obtainable by the minimum X-ray source current. The main application fields are lung cancer screening or pediatrics.

For an energy-integrating detector, filters are used for this purpose which reduce the X-ray intensity to such an extent that an examination is nonetheless possible in the ultra-low dosage range, for example, a tin filter is used at a tube voltage of 100 KV. There are currently no optimized filters for examinations in the ultra-low dosage range with spectrally sensitive detectors.

SUMMARY

In contrast, at least one embodiment of the present invention provides a filter and a method for the spectral filtration of X-rays for X-ray imaging via spectrally sensitive detectors which decreases or even overcomes at least one of the problems of the prior art described above.

At least one embodiment of the invention is directed to a filter for the spectral filtration of X-rays emanating from an X-ray source which are detected by an X-ray detector in at least two different spectral regions, wherein the filter only suppresses a particular part of the energy spectrum. At least one embodiment of the invention is further directed to a corresponding X-ray system and/or method. Developments and advantageous embodiments are each the subject of the claims.

Hereinafter, embodiments of the invention are described in relation to the devices as well as the method. Likewise, features, advantages or alternative embodiments mentioned in the process are also to be assigned to the other subject matters claimed and vice versa. In other words, objective claims (which, for example, are focused on one method) can also be developed with features which are described or claimed in connection with a device. The corresponding functional features of the method are embodied by corresponding objective modules or units.

A first embodiment of the invention relates to a filter for the spectral filtration of X-rays emanating from an X-ray source which cross an object under examination and are detected by an X-ray detector in at least two different spectral regions, wherein after crossing the object under examination, the X-rays have an energy spectrum which displays a characteristic distribution for the anode material of the X-ray source, wherein the filter is configured to suppress part of the energy spectrum comprising the focal point of the energy spectrum.

At least one embodiment of the invention according to another aspect also relates to an X-ray system, in particular a computer tomography device, comprising a filter according to at least one embodiment of the invention.

The X-ray system of at least one embodiment is an X-ray machine which is designed to record an individual or a multiplicity of X-ray projections from the same or different projection angles and/or projection directions. In a further embodiment of the invention the X-ray system can, for example, be designed as a computer tomograph, angiography system, projection radiography system or the like. In particular, the X-ray system may be a computer tomography device with a toroidal rotating frame or a C-arm X-ray machine which may be used for both one and the other type of recording.

The invention according to another embodiment relates to a method for the spectral filtration of X-rays emanating from an X-ray source which crosses an object under examination and is detected by an X-ray detector in at least two different spectral regions, wherein after crossing the object under examination the X-rays have an energy spectrum which displays a distribution characteristic of the anode material of the X-ray source, wherein a part of the energy spectrum comprising the focal point of the energy spectrum is suppressed.

The method may be performed by way of a filter according to at least one embodiment of the invention.

BRIEF DESCRIPTION OF THE DRAWINGS

The aforementioned properties, features and advantages of embodiments of the invention and the manner in which they are obtained will be clearer and more understandable with reference to the following description of the example embodiments, which are explained in more detail with reference to the diagrams. This description does not restrict the invention to these example embodiments. The diagrams show.

DETAILED DESCRIPTION OF THE EXAMPLE EMBODIMENTS

Figure 1:
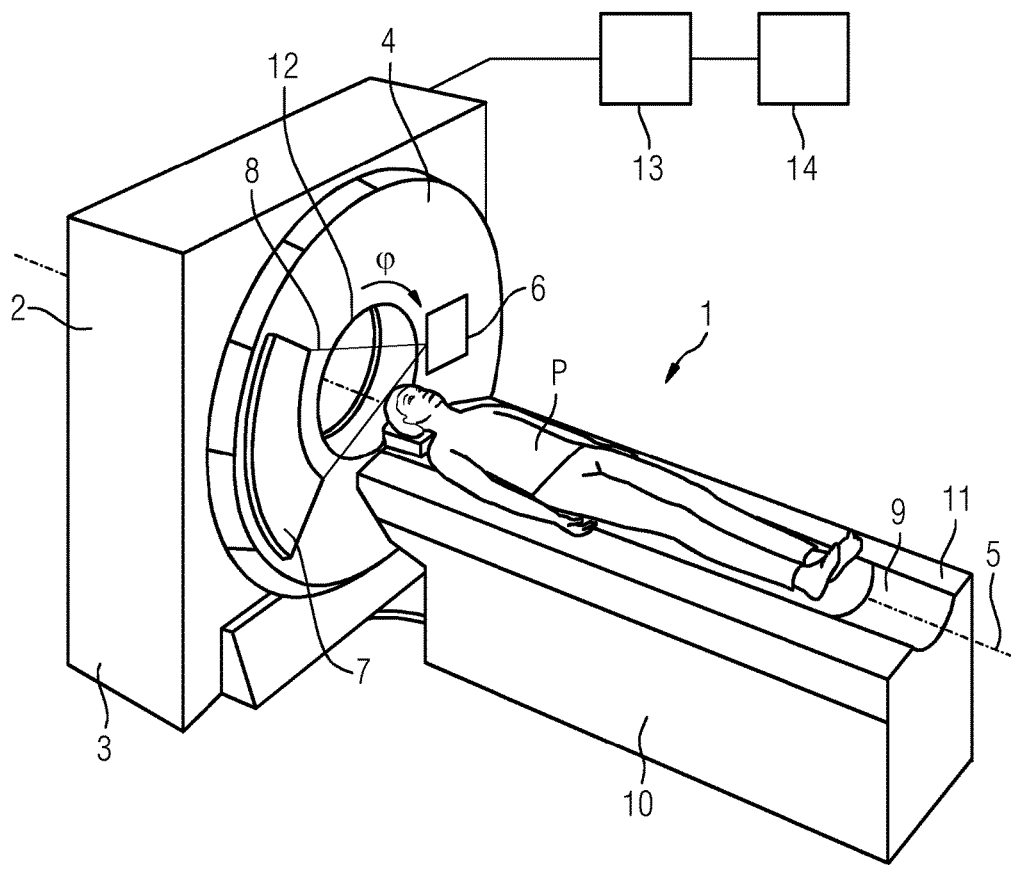
FIG. 1 An X-ray system comprising a filter according to the invention in an example embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or porcessors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

A first embodiment of the invention relates to a filter for the spectral filtration of X-rays emanating from an X-ray source which cross an object under examination and are detected by an X-ray detector in at least two different spectral regions, wherein after crossing the object under examination, the X-rays have an energy spectrum which displays a characteristic distribution for the anode material of the X-ray source, wherein the filter is configured to suppress part of the energy spectrum comprising the focal point of the energy spectrum.

In other words, the filter according to an embodiment of the invention is a filter with an absorption coefficient which is quantum energy-dependent to such an extent that it attenuates a range of the energy spectrum arranged around the focal point of the energy spectrum. Therefore, while certain spectral partial areas of the energy spectrum, e.g. the outer flanks of the energy spectrum, are only slightly attenuated by the filter or not at all, the center of the energy spectrum, in particular the partial area around the focal point of the spectrum, experiences a significant or at least considerable attenuation as a result of the filter.

An embodiment of the invention is based on the knowledge that by way of appropriate spectral pre-filtering of the energy spectrum, imaging with spectrally sensitive X-ray detectors can be improved, even with an imperfect detector response function. The energy thresholds of an energy-resolving detector are regularly adjusted such that approximately the same number of photons is detected in all the energy bins and/or energy windows. The range of the incident energy spectrum on the X-ray detector around the focal point of the spectrum may be at least partially detected in several energy bins. By way of targeted suppression of this spectral partial area in the incident energy spectrum, the signal component in the energy bins resulting from this spectral partial area can be suppressed and better separation of the energy channels obtained as a result.

The focal point of the energy spectrum designates the quantum energy within the incident energy spectrum on the detector, based on which, in statistical terms, both in the direction of lower energy values and in the direction of higher energy values, the same radiation intensity can be measured and/or the same number of X-ray quanta occurs within the energy spectrum.

The spectrum incident on the detector differs from the energy spectrum generated by the X-ray source insofar as the X-rays incident on the detector have already passed through an object under examination. The object under examination may be a patient or perhaps a phantom, e.g. a water equivalent with a diameter of 30 cm.

The spectrally selective attenuation of the filter is essentially based on the absorption of the X-ray quantum energy in the filter material on account of the interaction of X-rays and filter material.

An energy spectrum (before or after crossing an object under examination) is typically composed of a continuous retardation spectrum of electrons in the anode of the X-ray source and line spectra of the characteristic X-rays, the position of which within the spectrum depends on the material of the X-ray anode. The characteristic line spectra each correspond to the quantum energy which is released during the passage of an electron from an outer electron shell to an electron shell closer to the atomic nucleus.

An X-ray maximum of the characteristic X-rays corresponds to a characteristic line spectrum. An X-ray maximum may be an absolute or local maximum within the generated X-ray spectrum. The maximum energy of the photons in the spectrum is provided by the acceleration voltage connected to the X-ray anode. In some cases, the line spectra of the characteristic X-rays are close together compared to the width of the X-ray spectrum generated so that one or more of the X-ray maxima generate a similar or comparable signal in the spectrally sensitive detector.

In addition, the X-ray maxima are often in or close to the region of the focal point of the spectrum so that high peaks of intensity in the incident spectrum result in signal components in several energy channels of the detector. This hampers correct spectral separation. The inventors have now recognized that a filter which is configured to suppress part of the energy spectrum comprising the focal point of the spectrum results in the improved spectral resolution of the X-ray detector.

Due to the location of the characteristic X-ray maxima, the filter according to the invention can be embodied such that it suppresses at least one or more or all of the X-ray maxima of the characteristic X-rays, in particular one or more of the high-energy X-ray maxima.

In an embodiment of the invention, the filter has an absorption coefficient for X-rays which rises sharply with increasing X-ray quantum energy below the focal point of the energy spectrum. The significant increase in the absorption coefficient is preferably in the direct or immediate spectral vicinity of the focal point of the spectrum, e.g. within 5 keV and only extends over a small spectral range, e.g. from 0 keV to 5 keV. The significant increase in the absorption coefficient results in particularly advantageous suppression of the signal components caused by the central range of the energy spectrum on the spectrally resolved X-ray detector. While the filter lets the part of the energy spectrum below the focal point pass unimpeded or at least essentially in full, e.g. 60 percent to 100 percent, the X-ray quanta with energies above the focal point of the spectrum are largely absorbed in a partial area of the spectrum, e.g. 60 percent to 97 percent.

In some cases, depending on the anode material, the filter lets the characteristic line spectrum with the lowest energy pass, while it absorbs the X-ray quanta of at least one high-energy line spectrum almost completely. In other words, in some cases a significant increase in the absorption coefficient is found directly above the characteristic line spectra with the lowest energy.

In an advantageous development of an embodiment of the invention, the filter has an absorption coefficient for X-rays which decreases exponentially with increasing X-ray quantum energy above the part of the energy spectrum comprising the focal point of the energy spectrum. This embodiment of the filter results in strong absorption of the spectral partial area of the energy spectrum directly adjoining the focal point of the spectrum in the direction of higher energies, wherein in contrast more distant spectral partial areas are rapidly absorbed less strongly with increasing X-ray quantum energy.

According to an embodiment of the invention, the filter is configured to attenuate the intensity of the X-rays in the part of the energy spectrum comprising the focal point of the energy spectrum by five percent to 97 percent on average, e.g. by 30 percent. The simulations carried out by the inventors have revealed that such a spectral resolution of the incident X-rays by way of a spectrally sensitive X-ray detector is particularly good.

In an embodiment of the invention, the filter is configured to absorb a maximum of 30 percent of all X-ray source power. The loss of up to 30 percent of the X-ray source power can be offset by a corresponding increase in the X-ray source current and/or X-ray tube current. In this respect, the present invention is particularly appropriate for use in applications and/or examinations in the normal dosage range and therefore has a very wide range of applications in X-ray imaging.

In an alternative embodiment, the filter is configured to absorb 95 percent to 97 percent of the entire X-ray source power. An embodiment of the invention is therefore also suitable for use in the ultra-low dosage range, in particular for lung cancer screening or pediatrics, wherein spectral imaging in the ultra-low dosage range was not possible until now.

In a development of an embodiment of the invention, the filter can be moved into and/or out of the X-ray beam, wherein the filter has a different material thickness along the path of travel. In this manner, by way of an adjustment of the material thickness in the X-ray beam the filter effect can be adjusted to the present application and/or examination. Elaborate reconfiguration of a filter from one X-ray examination to the next or even changing from one X-ray system to another is advantageously omitted. For example, the design of the filter can be integral and stepped along the path of travel. Alternatively, the filter may also include two opposing filter elements that can be moved along the path of travel and are designed in steps or of a variety of likewise individually mobile, flat filter plates which can be superimposed.

According to another example embodiment, the filter may also be a permanently integrated part of an X-ray system which can only be replaced by professional service personnel.

In a further embodiment of the invention, the filter material has an atomic number between 70 and 74. The inventors have recognized that these materials are particularly suitable for use in computer tomography using typical energy spectra. Typically, with computer tomography a tungsten anode is used. Other anode types are naturally also possible.

For an energy spectrum which is generated in computer tomography with an X-ray beam source voltage of, for example, 140 kV, in a development of an embodiment of the invention the filter achieves particularly good spectral resolution by way of a spectrally sensitive detector if ytterbium is chosen as a filter material.

At least one embodiment of the invention according to another aspect also relates to an X-ray system, in particular a computer tomography device, comprising a filter according to at least one embodiment of the invention.

The X-ray system of at least one embodiment is an X-ray machine which is designed to record an individual or a multiplicity of X-ray projections from the same or different projection angles and/or projection directions. In a further embodiment of the invention the X-ray system can, for example, be designed as a computer tomograph, angiography system, projection radiography system or the like. In particular, the X-ray system may be a computer tomography device with a toroidal rotating frame or a C-arm X-ray machine which may be used for both one and the other type of recording.

The X-ray images may, for example, be generated during an, in particular, continuous rotation movement of a recording unit comprising an X-ray source and an X-ray detector interacting with the X-ray source. Alternatively, several X-ray images may be recorded in one projection direction while in the meantime the interacting X-ray source and X-ray detector are not moved.

An X-ray detector for a computer tomography device may be, for example, a line detector with several lines. An X-ray detector for a C-arm X-ray machine may be, for example, a flat-panel detector. For the purposes of at least one embodiment of the invention, the X-ray detector may be designed both for integration as well as for counting. In any case, it is an energy-sensitive X-ray detector. This enables and/or makes the simultaneous recording of X-ray image data easier with simultaneous flexibly applicable further processing options.

Energy-integrating X-ray detectors nowadays are mainly based on scintillators, for example, of $CsJ$ or $Gd_2O_2S$, which, for example, convert X-rays into comparatively low-energy radiation, for example, visible light. This light is converted into electric charge in matrices of photodiodes. These are then generally read out line by line by means of active control elements. The basic structure of these so-called indirect-conversion X-ray detectors is a scintillator, an active readout array of amorphous silicon or embodied in CMOS technology with a multiplicity of pixel elements (with a photodiode and switching element) and control and readout electronics (see, for example, M. Spahn, "Flat detectors and their clinical applications", Eur Radiol. (2005), 15: 1934-1947, the entire contents of which is hereby incorporated herein by reference). Integrating X-ray detectors do not discriminate against the incident radiation according to their quantum energy.

Energy-sensitive and/or energy-selective is understood to mean with spectral resolution and/or spectral separation. Energy-selective detectors are configured to classify incident radiation quanta according to their quantum energy. The advantage of these detectors is that they are suitable for the simultaneous generation of at least two X-ray datasets which differ in their quantum energy distribution.

Energy-selective detectors are, for example, quantum-counting detectors or integrating double layer detectors. A quantum-counting detector is typically a direct-conversion detector which directly converts an incident radiation quantum into an electrical signal by way of suitable detector material. Quantum-counting detectors can be operated with energy-resolution, wherein the energy resolution is adjustable by means of so-called binning.

In other words, almost any energy fields can be established with regard to which incident X-ray quanta can be classified. The at least two X-ray datasets are each formed by signals within one or more energy fields. The semiconductors cadmium telluride, cadmium zinc telluride or gallium arsenide or, in the case of a flat-panel detector, amorphous selenium or the like are particularly suitable as detector materials for quantum-counting detectors in medical computer tomography.

There is no limit to the use of quantum-counting, energy-selective X-ray detectors in embodiments of the invention. Both two as well as more energy bins and/or energy windows can be viewed simultaneously and subsequently evaluated.

A dual or double layer detector is designed to separate the incident radiation spectrum into a low-energy and a high-energy portion. The double layer detector is composed of two layers for this purpose. A detector layer facing the X-ray source measures radiation quanta of the incident radiation with low energy and assigns the measured signals to the first X-ray data set. It is penetrated by high-energy radiation. Photons with higher quantum energy are measured in the detector layer below and/or behind, in other words, facing away from the X-ray source and assigned to the second X-ray data set.

Typically, both detector layers comprise a scintillator and the double layer detector is therefore an indirect-conversion detector. Crystals such as cesium iodide, cadmium tungstate or ceramic materials such as, for example, gadolinium oxysulfide or the like are used as scintillation material. Double layer detectors are particularly suitable for the present invention if one of the energy thresholds between high-energy and low-energy radiation is close to or above the focal point of the energy spectrum and/or the rapidly increasing area of the absorption coefficient of the filter.

The invention according to another embodiment relates to a method for the spectral filtration of X-rays emanating from an X-ray source which crosses an object under examination and is detected by an X-ray detector in at least two different spectral regions, wherein after crossing the object under examination the X-rays have an energy spectrum which displays a distribution characteristic of the anode material of the X-ray source, wherein a part of the energy spectrum comprising the focal point of the energy spectrum is suppressed.

The method may be performed by way of a filter according to at least one embodiment of the invention.

In an embodiment of the invention, filtration is performed such that the X-rays are detected in the normal dosage range.

In another preferred embodiment of the invention, filtration is performed such that the X-rays are detected in the ultra-low dosage range.

The X-ray system 1 shown in FIG. 1 in the form of an X-ray computer tomograph comprises a gantry 2 with a stationary part 3 and with a part 4 rotatable around a system axis and/or z axis 5. In the case of the present example embodiment of the invention, the rotatable part 4 has an X-ray system which comprises an X-ray source 6 and an X-ray detector 7 which are arranged opposite each other on the rotatable part 4.

During the operation of the X-ray computer tomograph, X-rays 8 emanate from the X-ray source 6 in the direction of the X-ray detector 7, penetrate an object under examination P, here a patient, and are recorded by the X-ray detector 7 in the form of detector signals and/or measurement data. The X-ray detector 7 has a multiplicity of detector elements arranged in detector lines and detector columns, wherein the detector columns run in the direction of the z axis and the detector lines in the direction of cp and thus perpendicularly to the direction of z.

The X-ray computer tomograph is a multi-layer and/or multi-slice X-ray computer tomograph. In addition, the X-ray detector 7 is designed as a quantum-counting, energy-selective X-ray detector, i.e. it is configured to generate several, in other words, at least two measurement datasets which differ with regard to the respective X-ray quantum energies under consideration for each detector element. Furthermore, the X-ray system 1 has a couch 9 for the positioning of the object under examination P.

The couch 9 comprises a base 10 on which a patient table 11 is arranged for the actual positioning of the object under examination P. The patient table 11 can be adjusted relative to the base 10 in the direction of the system axis 5 such that together with the object under examination P it can be introduced into the aperture 12 of the gantry 4 which in the present case defines a cylindrical measuring field, for the recording of 2-D X-ray projections of the object under examination P, for example, in a spiral scan.

The computational processing of the 2-D X-ray projections recorded using the X-ray system 1 and/or the reconstruction of tomographic images, 3-D images or a 3-D dataset based on the 2-D X-ray projections takes place using an image processor 13 of the X-ray system 1 by means of which tomographic images or 3-D images can be displayed on an indicator device 14. Reconstruction by the image processor 13 can take place, for example, using the reconstruction algorithm of the Weighted Filtered Back Projection. The X-ray source 6 has a filter 17 according to an embodiment of the invention.

Figure 2:
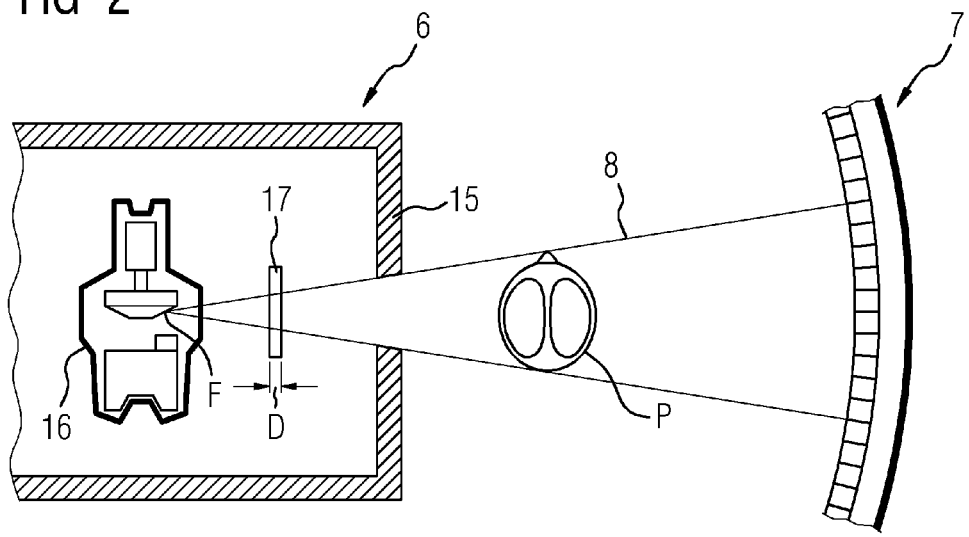
FIG. 2 An arrangement and embodiment of a filter according to the invention in an example embodiment.

FIG. 2 shows an example of the arrangement of the filter 17 inside the shutter case 15 of the X-ray source 6 according to a first example embodiment of the invention. X-rays 8 are generated by means of an X-ray tube 16, from the focal point F of which X-rays 8 emanate roughly conically and are emitted in the direction of the X-ray detector 7. The X-ray source 6 has a shutter 19 for focusing on the X-ray detector 7 and/or the object under examination P and/or body regions to be examined.

The filter 17 for the spectral filtration of X-rays 8 is arranged in the beam path directly behind the X-ray tube 16. In this example embodiment the filter has a basic rectangular or square shape and a constant thickness D. It may be assembled in the brackets provided, for example, instead of a tin filter, as a tin filter for the reduction of radiation intensity according to an embodiment the invention can be omitted. Both the thickness D as well as the shape of the filter and the material used may vary depending on the application and X-ray system 1 in which the filter is to be used. In FIG. 2 the filter is, for example, permanently assembled and can only be removed or replaced by trained service personnel.

Figure 3:
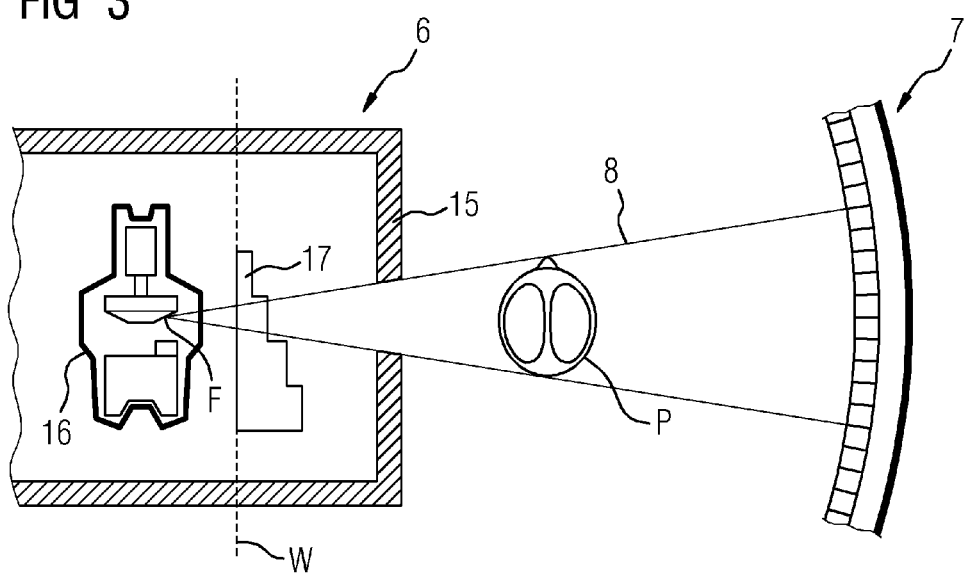
FIG. 3 An arrangement and embodiment of a filter according to the invention in another example embodiment.

FIG. 3 shows an alternative filter 17 according to another example embodiment of the invention. The filter 17 shown here is designed in steps and can be moved and/or slid along a path of travel W inside the case 16. A corresponding actuator and/or a drive motor (neither of which are shown) can be provided for this purpose. By this means different thicknesses D1, D2, D3, D4 of the filter can easily be configured, for example, if the energy spectrum configured for an X-ray examination is altered and/or another intensity attenuation is desired (for example, possibly changing from a normal dosage range to an ultra-low dosage range).

Figure 4A:
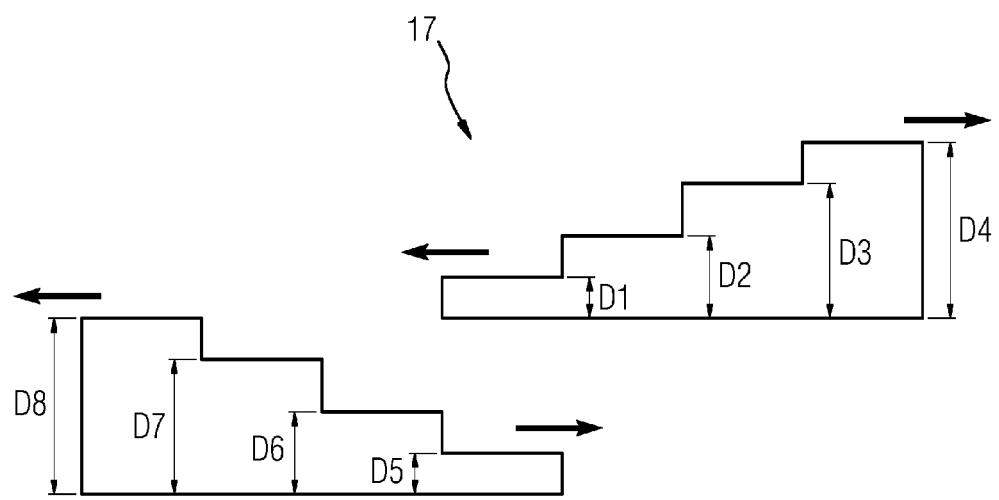
FIG. 4A Another embodiment of a filter according to the invention according to another example embodiment, FIG. 4B Another embodiment of a filter according to the invention according to another example embodiment, FIG. 5 A comparison of a filtered and unfiltered energy spectrum according to the invention, incident on an X-ray detector, FIG. 6 A comparison of unfiltered measurement data energy-selectively detected in two energy bins, FIG. 7 A comparison according to the invention of filtered measurement data energy-selectively detected in two energy bins in the normal dosage range, and FIG. 8 A comparison according to the invention of filtered measurement data energy-selectively detected in two energy bins in the ultra-low dosage range.
Figure 4B:
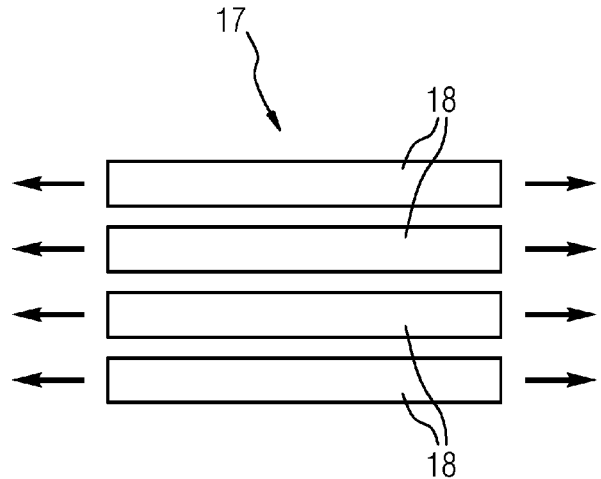

FIG. 4A and FIG. 4B show further embodiments of the shape of the filter 17 which can also be moved along the path of travel W (illustrated by the arrow) and are therefore equally suitable for the flexible adjustment of the thickness D of the filter material layer which the X-rays 8 must cross on their way to the object under examination P and/or X-ray detector 7. The filter 17 shown in FIG. 4A comprises two filter elements each of which has a stepped basic shape, wherein each step corresponds to a certain thickness D1, D2, D3, D4 and/or D5, D6, D7, D8, wherein the individual thicknesses can assume any and, in particular, divergent values for flexible adjustability. Both filter elements can be moved along the path of travel W.

By individually overlapping the filter element steps, the layer thickness of the filter material to be crossed by the X-rays can be adjusted. The filter 17 shown in FIG. 4B comprises several filter plates 18 of the same or different heights. Each of the filter plates 18 can be individually slid along the path of travel W. Together they form the filter 17. Any values of the layer thickness D of the filter material can be configured for the X-rays 8 by means of any combination of plates 18 in the beam path.

Other filter 17 shapes are also possible.

Figure 5:
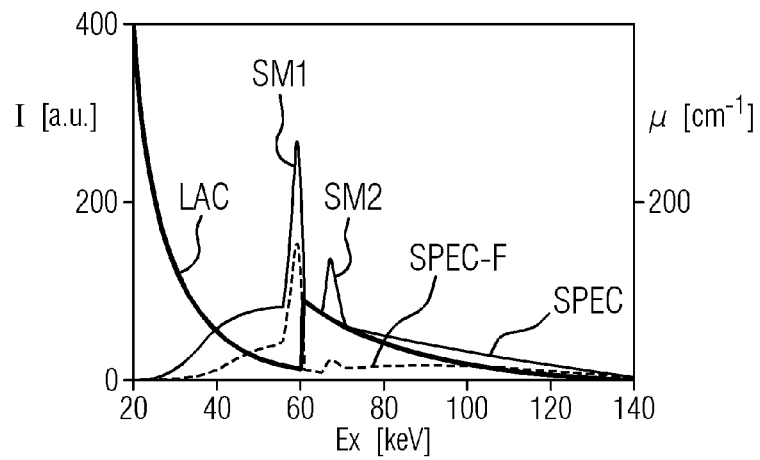

FIG. 5 shows the intensity I of an unfiltered X-ray spectrum SPEC incident on an X-ray detector. It was generated by means of an X-ray source 6 comprising an X-ray tube with a tungsten anode at a tube voltage of 140 kV and passed through a phantom in the form of a water equivalent with a diameter of 30 cm. In contrast, the intensity I of the corresponding X-ray spectrum SPEC-F filtered with a filter 17 is shown. Such X-ray beam sources 6 and a tube voltage of 140 kV are typically used in computer tomography systems. Other anode materials can also be used, if applicable in combination with another filter material, for example, molybdenum or rhodium are used in mammography anodes.

The filter 17 used here consists of the material ytterbium (Z=70). The total X-ray output was reduced to 40 percent by the filter 17. A filter with a thickness D of 0.265 mm was used for this purpose. At approx. 58 keV, the unfiltered spectrum displays the lowest X-ray quantum energy of the characteristic X-rays of the anode material, an X-ray maximum SM1 and/or a line spectrum corresponding to the K-alpha line of tungsten. At approx. 68 keV, it displays a further X-ray maximum SM2 with the next highest X-ray quantum energy corresponding to the K-beta line of tungsten.

It goes without saying that different anode materials have different energy spectra. The LAC path of the linear attenuation coefficient μ of ytterbium is also compared. At approx. 60 keV and therefore just below the focal point of the X-ray spectrum, this displays a sharp increase before then decreasing exponentially again.

In this example embodiment the significant increase is therefore directly above the K-alpha line. Directly below the sharp increase at 60 keV the attenuation coefficient LAC is only just above zero. In other words, while the X-ray spectrum around the K-beta line comprising the K-beta line is almost completely absorbed by the filter material, the K-alpha line only experiences minor attenuation. This can be read off with the aid of the filtered X-ray spectrum SPEC-F, in which the K-beta line now only appears strongly suppressed, whereas the K-alpha line has only experienced attenuation of approximately one third by the filter 17.

In particular, as a result of undesired effects such as charge sharing, K-escape and accompanying fluorescence shifts, the region around the focal point of the energy spectrum and at present in particular causes the tightly adjacent K-lines in spectral imaging in the various energy bin signal components. This overlapping of the information in the individual energy bins can be minimized and the spectral resolution of the X-ray detector increased as a result if the central region of the X-ray spectrum or here the region around the K-beta line is filtered as described. In other words, the additional use of the filter 17 improves spectral separation.

Figure 6:
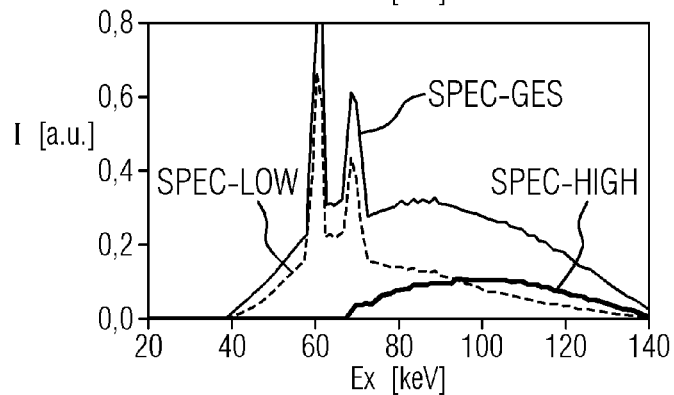

FIG. 6 shows an unfiltered X-ray spectrum SPEC-GES of a tungsten anode with a tube voltage of 140 kV recorded on the X-ray detector 7 and compares this with the detector signals recorded in two energy bins, likewise in the form of X-ray spectra SPEC-LOW and SPEC-HIGH, wherein for SPEC-LOW a threshold value of 22.5 keV and for SPEC-HIGH a threshold value of 67.5 keV was configured on the X-ray detector 7. A significant overlap of the two detected spectra is discernible, ranging from quantum energies of barely 70 keV to 140 keV. This overlap is primarily caused by the aforementioned effects and impairs the significance of the individual energy channels. As a result, these are only partially suitable for further evaluation, e.g. material breakdown.

Figure 7:
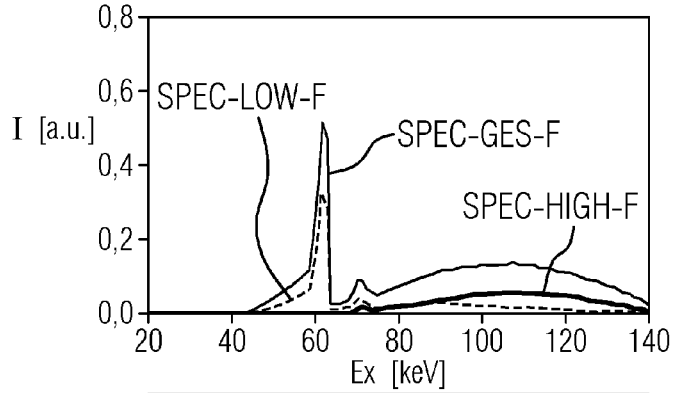

In FIG. 7, the X-ray spectrum SPEC-GES-F generated as in FIG. 6 and filtered by means of an ytterbium filter is compared with the X-ray spectra of two energy bins SPEC-LOW-F and SPEC-HIGH-F. The thickness of the filter material here is D=0.265 mm. The threshold values configured here for the energy bins are 27.5 keV and 62.5 keV. It is clearly recognizable that the signal component caused by the overlap and contained in both energetically separately detected spectra is significantly reduced by filtration.

As the irradiated spectrum alters with the thickness D of the filter material, the configuration of the energy threshold is an optimization task which, for example, can be solved empirically.

Figure 8:
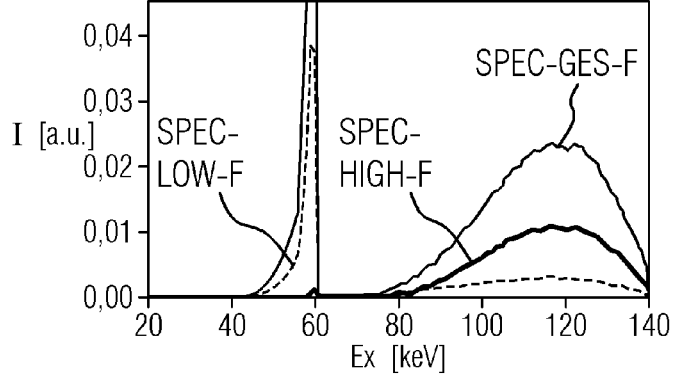

Finally, FIG. 8 shows an application in the ultra-low dosage range. Likewise, the X-ray spectrum SPEC-GES-F generated as in FIG. 6 and filtered by means of ytterbium filter is compared with the X-ray spectra of two energy bins SPEC-LOW-F and SPEC-HIGH-F. The thickness of the filter material here is D=1.17 mm. The threshold values configured for the energy bins here are 32.5 keV and 62.5 keV. By using a thicker filter 17, the signal component caused by the overlap and contained in both energetically separately detected spectra can be further reduced and spectral separation further improved.

Although the invention was illustrated in more detail by the preferred example embodiment, the invention is not restricted by the disclosed examples and other variations can be deduced by a person skilled in the art without departing from the scope of the invention. In particular, where technically possible and reasonable, features of the example embodiments described can be interchanged.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A medical x-ray computed tomography device, comprising:
   an x-ray source to produce and emanate X-rays;
   an energy-selective X-ray detector to detect the X-rays; and
   a filter for the spectral filtration of X-rays emanating from an the X-ray source which cross an object under examination and are detectable by the X-ray detector in at least two different spectral regions, wherein after crossing the object under examination, the X-rays have an energy spectrum which displays a characteristic distribution for an anode material of the X-ray source, the filter being configured to suppress part of the energy spectrum including a focal point of the energy spectrum, the filter including an absorption coefficient which relatively increases, for X-rays below a part of the energy spectrum including the focal point of the energy spectrum, with relatively increasing X-ray quantum energy, wherein the relative increase of the absorption coefficient of the filter is directly above a K-alpha line of the anode material.

2. The medical x-ray computed tomography device of claim 1, wherein the absorption coefficient of the filter relatively decreases exponentially, for X-rays above a part of the energy spectrum comprising the focal point of the energy spectrum, with relatively increasing X-ray quantum energy.

3. The medical x-ray computed tomography device of claim 1, wherein the filter is configured to attenuate intensity of the X-rays, in the part of the energy spectrum including the focal point of the energy spectrum, by five to 97 percent on average.

4. The medical x-ray computed tomography device of claim 1, wherein the filter is configured to absorb a maximum of 30 percent of a total power of the X-ray source.

5. The medical x-ray computed tomography device of claim 1, wherein the filter is configured to absorb 95 percent to 97 percent of a total power of the X-ray source.

6. The medical x-ray computed tomography device of claim 1, wherein the filter is movable at least one of into and out of the X-ray beam, and wherein the filter includes a different material thickness along a path of travel.

7. The medical x-ray computed tomography device of claim 1, wherein a material of the filter has an atomic number between 70 and 74.

8. The medical x-ray computed tomography device of claim 1, wherein a material of the filter is ytterbium.

9. A method for spectral filtration, via a filter of an x-ray computed tomography device, of X-rays emanating from an X-ray source of the x-ray computed tomography device, which cross an object under examination and are detectable by an X-ray detector of the x-ray computed tomography device in at least two different spectral regions, the X-rays, after crossing the object under examination, including an energy spectrum which displays a characteristic distribution for an anode material of the X-ray source, the method comprising:
performing the spectral filtration of the X-rays, the spectral filtration including suppressing, via the filter, a part of the energy spectrum including a focal point of the energy spectrum, the filter including an absorption coefficient which relatively increases, for X-rays below the part of the energy spectrum including the focal point of the energy spectrum, with relatively increasing X-ray quantum energy, wherein the relative increase of the absorption coefficient of the filter is directly above a K-alpha line of the anode material.

10. The method of claim 9, wherein the performing of the spectral filtration includes detecting the X-rays in a dosage range that is relatively normal.

11. The method of claim 9, wherein the performing of the spectral filtration includes detecting the X-rays in a relatively ultra-low dosage range, relative to a normal dosage range.

12. The method of claim 9, wherein the absorption coefficient of the filter relatively decreases exponentially, for X-rays above the part of the energy spectrum including the focal point of the energy spectrum, with relatively increasing X-ray quantum energy.

13. The method of claim 9, wherein the filter is configured to attenuate intensity of the X-rays in the part of the energy spectrum including the focal point of the energy spectrum by five to 97 percent on average.

14. The method of claim 9, wherein the filter is configured to absorb a maximum of 30 percent of a total of the power of the X-ray source.

15. The method of claim 9, wherein the filter is configured to absorb 95 percent to 97 percent of a total of the power of the X-ray source.

16. The method of claim 9, wherein the filter is movable at least one of into and out of a beam of the X-rays, and wherein the filter includes a different material thickness along a path of travel.

17. The method of claim 9, wherein a material of the filter has an atomic number between 70 and 74.

18. The method of claim 9, wherein a material of the filter is ytterbium.

19. The method of claim 9, wherein the filter includes an absorption coefficient which is quantum energy-dependent, and wherein the performing of the spectral filtration of the X-rays includes relatively greatly attenuating a range of the energy spectrum arranged around the focal point of the energy spectrum and relatively slightly attenuating a range of the energy spectrum near an edge of the energy spectrum.

20. The medical x-ray computed tomography device of claim 1, wherein the filter includes an absorption coefficient which is quantum energy-dependent, and wherein the filter is configured to relatively greatly attenuate a range of the energy spectrum arranged around the focal point of the energy spectrum and relatively slightly attenuate a range of the energy spectrum near an edge of the energy spectrum.

21. The method of claim 9, wherein the filter includes an absorption coefficient which is quantum energy-dependent, and wherein the performing of the spectral filtration of the X-rays includes relatively greater attenuating of the energy spectrum relatively near the focal point of the energy spectrum and relatively slight attenuating of the energy spectrum relatively far from the focal point of the energy spectrum.

22. The medical x-ray computed tomography device of claim 1, wherein the filter includes an absorption coefficient which is quantum energy-dependent, and wherein the filter is configured to relatively greatly attenuate the energy spectrum relatively near the focal point of the energy spectrum and relatively slightly attenuate the energy spectrum relatively far from the focal point of the energy spectrum.

* * * * *